(12) United States Patent
McMillan et al.

(10) Patent No.: US 12,318,323 B1
(45) Date of Patent: Jun. 3, 2025

(54) EXTENDABLE FRACTURE ORTHOSIS

(71) Applicant: WEBER ORTHOPEDIC, L.P., Santa Paula, CA (US)

(72) Inventors: Jamie McMillan, Billings, MT (US); Jeremy Schillig, Mansfield, TX (US); Martha Ortega, Bedford, TX (US); James Buckhout, Hampton, NJ (US); John Hely, Roanoke, TX (US)

(73) Assignee: Weber Orthopedic, L.P., Santa Paula, CA (US)

( * ) Notice: Subject to any disclaimer, the term of this patent is extended or adjusted under 35 U.S.C. 154(b) by 81 days.

(21) Appl. No.: 16/905,826

(22) Filed: Jun. 18, 2020

(51) Int. Cl.
*A61F 5/30* (2006.01)
*A61F 5/058* (2006.01)
*A61F 5/01* (2006.01)

(52) U.S. Cl.
CPC ...... *A61F 5/05866* (2013.01); *A61F 5/05875* (2013.01); *A61F 5/30* (2013.01); *A61F 2005/0172* (2013.01)

(58) Field of Classification Search
CPC .............. A61G 13/0045; A61H 1/0277; A61H 1/0285; A61H 1/0288; A61F 13/107; A61F 5/373; A61F 5/3738; A61F 5/30; A61F 5/05875; A61F 5/05866; A61F 2005/0172
USPC ........................................................ 602/21
See application file for complete search history.

(56) References Cited

U.S. PATENT DOCUMENTS

| | | | | |
|---|---|---|---|---|
| 3,256,880 A | * | 6/1966 | Caypinar | ................. A61M 5/52 128/877 |
| 3,938,509 A | * | 2/1976 | Barber | ................. A61F 5/05866 602/21 |
| 4,201,203 A | * | 5/1980 | Applegate | ............. A61F 5/0109 2/24 |
| 4,854,309 A | | 8/1989 | Elsey | |
| 4,881,533 A | | 11/1989 | Teurlings | |
| 5,358,471 A | | 10/1994 | Klotz | |
| 5,725,490 A | | 3/1998 | Conran | |

(Continued)

FOREIGN PATENT DOCUMENTS

WO   PCT/GB93/01395 A1   1/1994
WO   PCT/US2004/001165 A2   8/2004

OTHER PUBLICATIONS

Debby Schwartz, 6 Ins and Outs for Using Hook-and-Loop Straps in Orthotic Fabrication, May 14, 2019, Orfit (Year: 2019).*

(Continued)

*Primary Examiner* — Alireza Nia
*Assistant Examiner* — Michael Milo
(74) *Attorney, Agent, or Firm* — Paul Y. Feng; One LLP

(57) ABSTRACT

An elbow-forearm-wrist-hand-finger orthosis having a telescoping and detachable palm/finger rest extending from a wrist-forearm gauntlet wherein the distance between the two is adjustable. The forearm and wrist gauntlet includes a clamshell configuration with an internal stiffener and a volar pocket. The palm/finger rest has a rigid bar extending therefrom that is slidably disposed within the volar pocket for wearer-adjustable extension out of and retraction into the pocket. Several retention straps are disposed about the palm/finger rest and the gauntlet. The gauntlet bottom and the palm/finger rest include curved sections to orient the wrist in a neutral position and the fingers in a relaxed position.

17 Claims, 2 Drawing Sheets

(56) References Cited

U.S. PATENT DOCUMENTS

| | | | | |
|---|---|---|---|---|
| 5,733,249 | A | * | 3/1998 | Katzin .................. A61F 5/0106 602/21 |
| 5,916,186 | A | * | 6/1999 | Turto .................... A61F 5/0118 602/20 |
| 6,443,918 | B1 | * | 9/2002 | Wang ................. A61F 5/05866 602/5 |
| 9,737,431 | B1 | | 8/2017 | Weber et al. |
| 9,782,285 | B1 | * | 10/2017 | Weber .................. A61F 5/0118 |
| 2005/0101897 | A1 | * | 5/2005 | Froom ............... A61F 5/05866 602/21 |
| 2005/0177081 | A1 | * | 8/2005 | Scheinberg ........... A61F 5/0118 602/5 |
| 2005/0240140 | A1 | | 10/2005 | Nelson et al. |
| 2010/0113997 | A1 | * | 5/2010 | Bauerfeind ........... A61F 5/0118 602/21 |
| 2011/0282253 | A1 | | 11/2011 | Menon et al. |
| 2013/0041302 | A1 | | 2/2013 | Williams |
| 2014/0083437 | A1 | * | 3/2014 | Hall ...................... A61F 5/3723 128/879 |
| 2017/0027737 | A1 | * | 2/2017 | Boileau ................. A61F 5/3723 |

OTHER PUBLICATIONS

Bort Swiss Orthopedic Supply, Bort Soft Hand Wrist Brace With Adjustable Finger Support, For Arthritis & Carpal Tunnel, web page dated Jan. 30, 2020.

saebo.com, Saebostretch stroke splint, web page dated Jan. 30, 2020.

Alimed, DynaPro Finger Flex Orthosis, web page dated Jan. 30, 2020.

Alimed, Comfyprene Hand/Wrist Orthosis, web page dated Jan. 29, 2020.

dme-direct.com, Bledsoe Telescoping Elbow Brace, web page dated Jun. 5, 2020, copyright 2018.

* cited by examiner

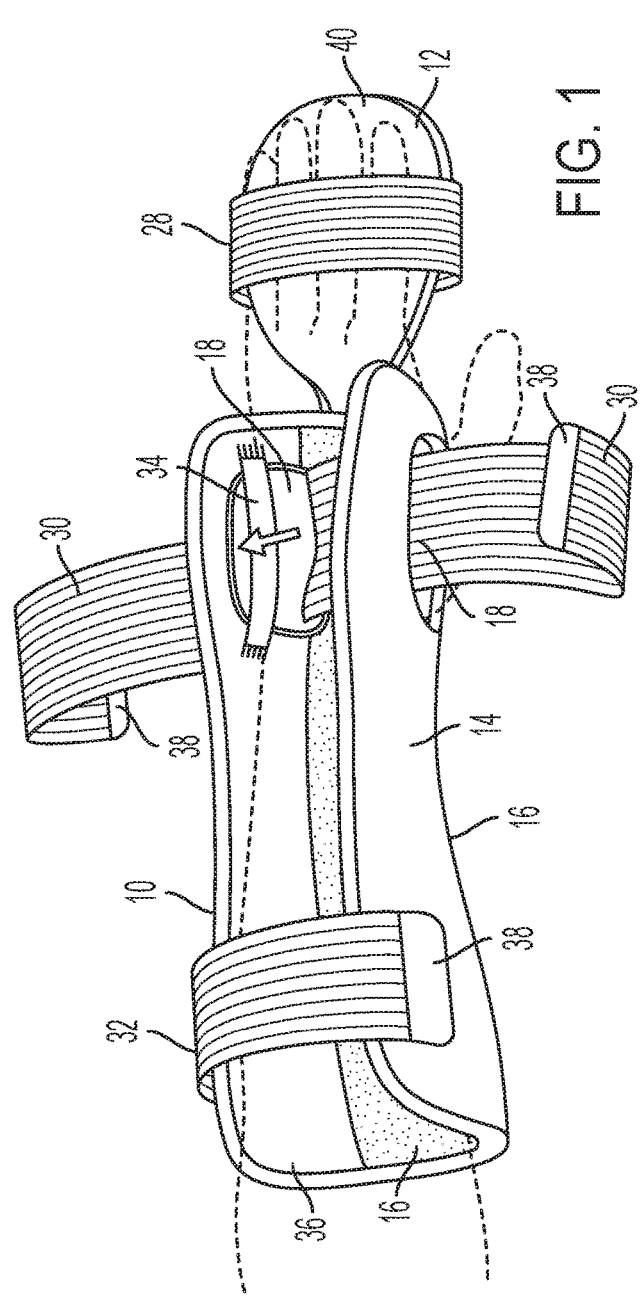
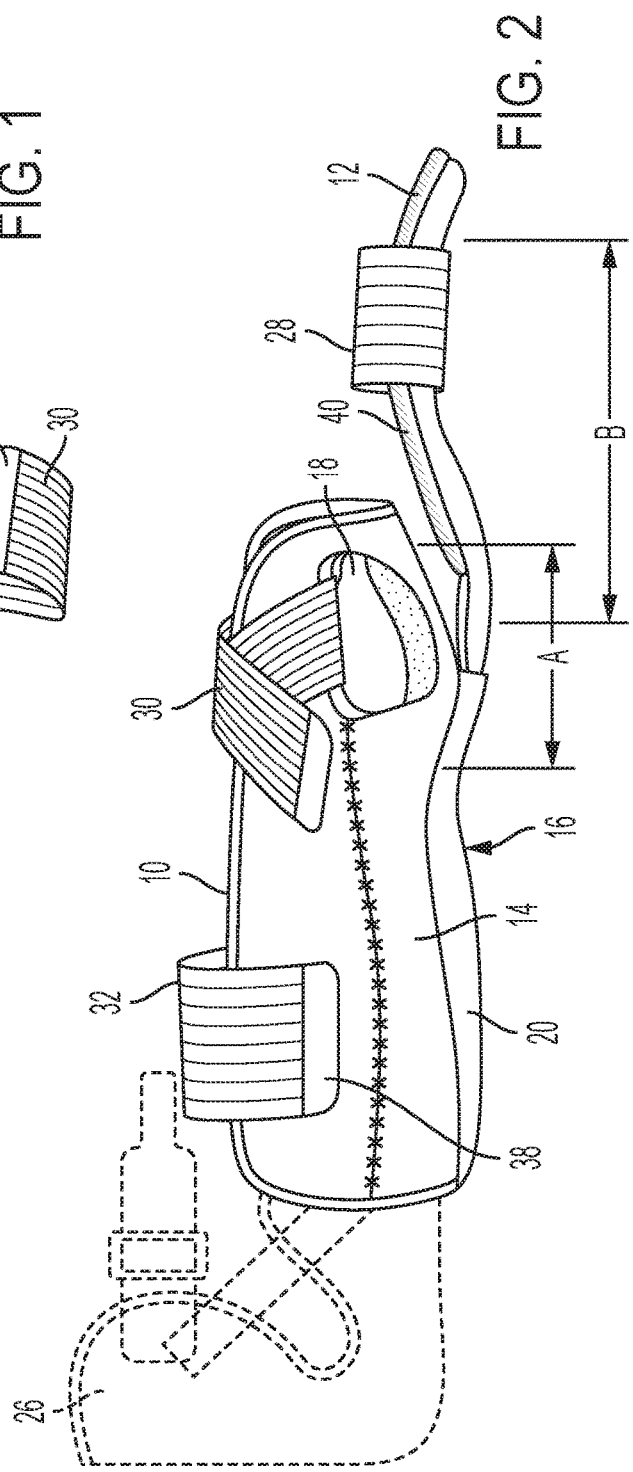

EXTENDABLE FRACTURE ORTHOSIS

FIELD OF THE INVENTION

The present invention relates to an orthopedic brace. In particular, the present invention relates to a length-adjustable elbow-forearm-wrist-hand-finger orthosis to immobilize fractures to the hand, wrist, forearm, elbow or like injuries.

BACKGROUND

Typical indications for applying a wrist-hand orthosis to a patient include carpal tunnel syndrome, an injury resulting from a stroke, sprains, strains, and wrist and hand contractures. In contrast, fracture orthoses protect and minimize deformity in the case of a non-displaced fracture. Fracture orthoses are designed to stabilize and minimize movement of the fractured area to promote and stimulate bone growth, resulting in less recovery time.

One such fracture orthosis is a sugar tong cast or splint. Each sugar tong cast is custom made to fit each patient using components such as adhesive tape, gauze, strips of casting tape, and bandage, which then must be cut to size with scissors and pieced together. Strips of splint or casting material must be selected for the correct dimensions and its length cut to match the patient's arm, moistened sufficiently but not overly, applied precisely to the patient's hand/wrist/forearm/elbow regions. The technician must also carefully wrap and smooth out folds and creases, etc., to ensure efficacy and comfort for the patient. Each cast requires training, skill, and time to fabricate and customize for proper fitment to each patient.

SUMMARY OF THE INVENTION

The present invention in a preferred embodiment is directed to an elbow forearm, wrist, hand, finger orthosis, comprising two modular components, namely, a forearm and wrist gauntlet in a clamshell configuration having a rigid bottom and a proximal end and a distal end, and a detachable and telescoping palm/finger rest. The clamshell has an open top and a closed bottom, which open top facilitates easy application of the gauntlet to a patient's injured forearm, wrist, joint, or limb.

The rigid bottom of the gauntlet includes a first curved profile accommodating a wrist neutral application, while the distal end includes at least one thumb opening. The clamshell is at least partially covered in softgoods, UBL, pile, or hook-and-loop type fabric. The underside of the gauntlet includes a volar pocket extending along a length thereof with a distal opening or slot. The palm/finger rest has an ovoid shape with a straight, rigid, bar extending proximally therefrom. The bar is slidably disposed within the pocket for adjustable extension out of the pocket and retraction into the pocket so the patient, physician, or technician may adjust a distance or gap between the palm/finger rest and the gauntlet.

The bar and palm/finger rest may include a first curved profile to accommodate a wrist neutral application and a second curved profile to accommodate a fingers-relaxed disposition. The bar is malleable, and the gauntlet bottom may include a malleable stiffener. As such, the first and second curved profiles in the orthosis can be further bent into a desired shape to suit a patient's unique anatomy and injury.

This distance adjustment is advantageous, because it enables daily, gross or minute adjustment of the gap by the patient, physician, or technician to address swelling in the injured region. It also customizes the orthosis to the wearer's hand/wrist size and as physical conditions change, which improves comfort for the wearer and minimizes edema during the recuperation period. Furthermore, the modular orthosis includes a step-down feature in that the palm/finger rest can be completely detached from the wrist gauntlet. This allows the patient to continue wearing the gauntlet only for the remainder of the recuperation period.

In alternative embodiments of the elbow-forearm-wrist-hand-finger orthosis, the bar of the palm/finger rest includes an anchor that attaches to the gauntlet to maintain the distance of the palm/finger rest from the gauntlet. The anchor may include hook-and-loop fasteners in the form of a patch or strip. For further comfort of the wearer, padding at least partially covering the palm/finger rest may be included.

The orthosis has a first strap disposed circumferentially about the palm/finger rest to hold the wearer's hand in place on the palm/finger rest. A second strap is disposed about the gauntlet, passing through the thumb opening and wrapping around the dorsum and gauntlet. The straps are preferably made from stretchable, open-knit fabric to help with compression and stabilization of the injury. An optional third strap compresses the open top of the clamshell around the forearm region.

The distal end of the gauntlet clamshell may include opposed thumb openings for left-hand and right-hand applications. The two thumb openings allow the same orthosis to be worn on either the left or right hand of the patient. This reduces the inventory held in stock by the clinic or reseller by one-half.

BRIEF DESCRIPTION OF THE DRAWINGS

FIG. 1 is a perspective view of a preferred embodiment elbow-forearm-wrist-hand-finger orthosis applied to a patient's left hand, shown in phantom lines.

FIG. 2 is a side elevational view of the elbow-forearm-wrist-hand-finger orthosis of FIG. 1 with an optional elbow orthosis.

DETAILED DESCRIPTION OF THE PREFERRED EMBODIMENTS

Figure 3:
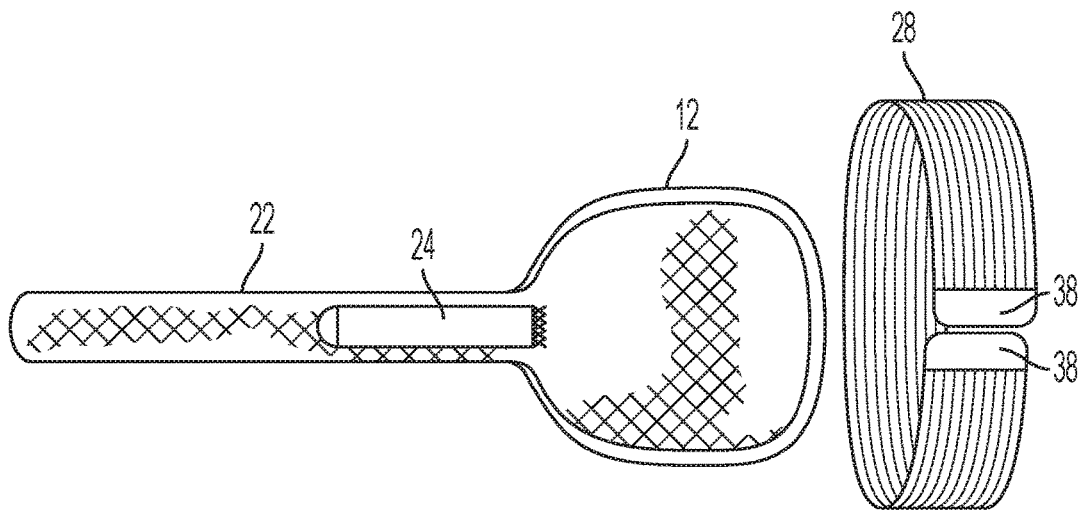
FIG. 3 is a bottom view of the palm/finger rest and bar extending therefrom.

The preferred embodiment fracture orthosis and variations thereof are indicated for ulna, scaphoid, distal radius, wrist and elbow fractures; triangular fibrocartilage complex (TFCC) injury and repair; multi-trauma injuries; crush injuries; lacerations; acute finger, wrist, forearm, or elbow injuries; and post-operative immobilization.

FIG. 1 depicts a preferred embodiment of an elbow-forearm-wrist-hand-finger orthosis 10 having two modular, discrete components-a forearm/wrist gauntlet 14 and a telescoping and detachable palm/finger rest 12. The orthosis 10 is shown as applied to a wearer's left hand (palm facing down in the drawing, represented by dashed lines) with the wrist flexion in neutral. The palm and digits are supported by a palm/finger rest 12. The palm/finger rest 12 features an optional padded layer 40 where the palm and digits come in contact. The wrist and forearm are supported by a forearm/wrist gauntlet 14 having preferably a clamshell configuration with an open top and a closed bottom. The palm/finger rest 12, having an ovoid or similar shape, extends from the distal end of the gauntlet 14 when the two components are joined. Generally, the palm/finger rest 12 and forearm/wrist gauntlet 14 include malleable material so they can be bent into shape to allow for alternative positions for the various maladies the orthosis is used to treat.

In FIG. 1, portions of the palmar region and digits rest on the palm/finger rest 12. Other portions of the palmar region are supported by the gauntlet 14. At the distal end of the gauntlet 14 are opposed thumb openings 18 to accommodate the wearer's thumb. There are two openings 18 so the same orthosis 10 may be applied for left-hand or right-hand applications. This saves on inventory that the clinic must keep in stock. The fabric immediately distal to the thumb openings 18 is soft, padded, and may be extended to wrap around as a thumb spica if desired.

Figure 4:
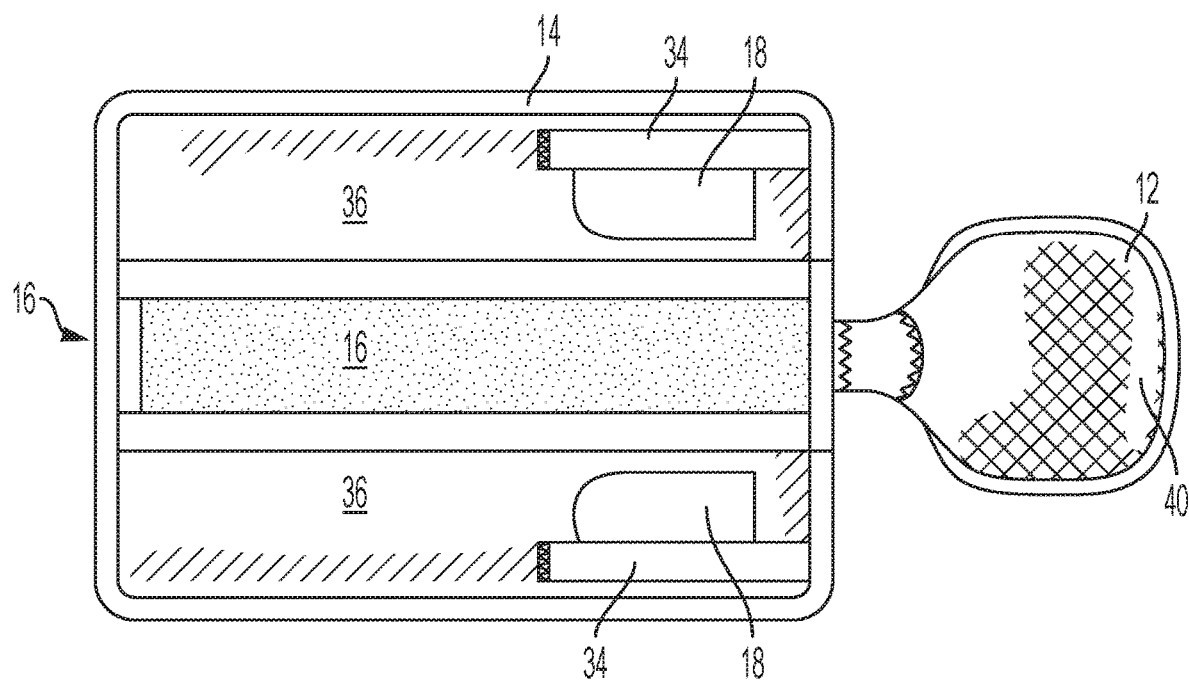
FIG. 4 is a top plan view of the elbow-forearm-wrist-hand-finger orthosis with the clamshell gauntlet opened flat.

The gauntlet 14 preferably has a shell configuration and more preferably a clamshell configuration with an open top and a closed bottom. The open top of the clamshell allows easy application of the orthosis to a pressure-sensitive and injured joint along with loose or tight compression adjustment to accommodate swelling. FIG. 4 shows the clamshell 14 in a top plan view with the opposed side panels 36 spread apart and flattened exposing the bottom 16. The interior of the panels 36, bottom 16 and other parts of the gauntlet 14 may be softly padded for improved comfort. The opposed pair of thumb openings 18 can be seen proximate the distal end. The palm/finger rest 12 can be seen extending from underneath the gauntlet 14.

Preferred construction materials for the gauntlet clamshell 14 include rigid EVA (ethylene vinyl acetate) foam or other semi-rigid thermoplastic foam with fabric laminated to both sides of the panels 36 and bottom 16. The exterior of the clamshell 14 is preferably covered in a softgoods, UBL (unbroken loop), or like pile fabric that can receive VEL-CRO® hooks, or have loop swatches added to make it VELCRO® hook receivable. The peripheral edges of the clamshell 14 are rounded and blunted to avoid abrasion to the skin.

In an alternative embodiment, the clamshell is made from a laminate with semi-rigid EVA foam encasing a malleable aluminum (aluminum in the middle to help retain a molded but formable shape) with fabric on both outer sides of the EVA foam. Such a laminate would be constructed with fabric (UBL or other), EVA foam or other semi-rigid foam, malleable aluminum strip(s), EVA foam or other semi-rigid foam, fabric (UBL or other). The laminate layers may be glued, stitched, sewn, welded, riveted, or likewise joined together.

The preferred embodiment clamshell or gauntlet 14 has a curved and rigid bottom 16 for stabilizing the ulna and radius, and to place the wrist flexion in neutral as seen in FIG. 1. This curved section, labeled "A," is best seen in the side elevational, profile view of the orthosis 10 in FIG. 2. The curvature A is pre-formed at the factory but may be bent as needed when the orthosis is applied to the patient. The rigidity in the clamshell bottom may be achieved by an insert, a spine, a stiffener, or the like stitched or embedded into the bottom 16 of the clamshell 14. The insert, spine or stiffener may be a strip of malleable aluminum, steel, plastic, wire mesh, or may be metal rods and the like. The degree of stiffness should be measured from a clinical standpoint, i.e., sufficient to support and stabilize a post-injury or post-operative forearm or wrist but still malleable by hand.

At the bottom 16 of the clamshell 14 is an elongated volar pocket 20 that extends along the length of the clamshell 14 with an open distal end/slot and a closed proximal end. The palm/finger rest 12 includes a preferably straight bar or arm 22 ("straight" from a plan view) extending from its proximal end as seen in FIG. 3. The bar 22 is preferably covered in softgoods, UBL, or like pile fabric that serves as attachment surfaces for the VELCRO® hook component.

In the side profile view of FIG. 2, the bar 22 may include one or more curves along sections labeled "A" and "B." The serpentine curvature A and B in the bar 22 facilitates the wrist neutral flexion (section A) and fingers-relaxed disposition (section B) with a natural finger curl while resting on the palm/finger rest 12. The curvature profile B in the bar may extend into the palm/finger rest 12 as seen in FIG. 2, or only be present in the palm/finger rest region and not in the bar. Indeed, profile curvatures A and B may be omitted completely from the bar in an alternative embodiment. The profile curvatures A and B in the orthosis 10 are present to enhance post-op recuperation.

Preferably, the straight bar 22 and palm/finger rest 12 are constructed from an integral piece of aluminum, steel, plastic, or other malleable materials. The curved sections A and B in the bar 22 and palm/finger rest 12 are pre-formed at the factory, but may be bent to their final shape when applied to the patient to accommodate various injuries for which the orthosis 10 is intended to treat.

The straight bar 22 is slidably inserted through the slot into the volar pocket 20 to join the palm/finger rest 12 to the gauntlet 14. This sliding bar 22 allows the distance or gap between the palm/finger rest 12 and gauntlet 14 to be quickly and easily adjusted to a longer or shorter length to accommodate post-op swelling in the wrist, hand, finger, etc. As the swelling increases or subsides, the distance or gap can be adjusted again and again as needed. This ensures comfort and minimizes post-op pain for the patient. It can be adjusted by the patient without need for a return visit to the clinic. Furthermore, the sliding bar 22 ensures that the orthosis 10 can be customized to match a patient's unique anatomy, e.g., larger hand with long digits. Other means for slidably adjusting the distance between the gauntlet and palm/finger rest include the bar sliding along a track or grooves embedded inside the gauntlet, or a rod replacing the bar that telescopes from a receiving pipe embedded inside the gauntlet.

When no longer needed, the palm/finger rest 12 can be slid out of the volar pocket 20 and completely detached from the gauntlet 14. The patient then continues wearing the gauntlet only for the remainder of his or her injury rehabilitation.

In the bottom view of the palm/finger rest 12 in FIG. 3, the bar 22 includes an optional anchor 24. The anchor 24 is preferably an elongated strip of the hook VELCRO® component stitched to the bar at one end (preferably the distal end), with the opposite (proximal end) end free to be peel away from the underlying softgoods, UBL, or pile fabric. Once the gap distance is set for the comfort of the wearer, the free end of the anchor 24 can be tamped down to the gauntlet 14, thereby immobilizing the relative movement between the two. In an alternative embodiment, the anchor includes a plastic strip with adjustment holes and pins extending from the gauntlet and bar, such that the two pins fit into their respective holes in the strip affixing a preselected distance. Also, the interior of the pocket 20 may include pile type material that rubs against the pile fabric covering of the bar 22, so if there is a tight fit inside the pocket 20, there is sufficient friction between the two to hold the palm/finger rest 12 in place relative to the gauntlet 14. However, with sufficient effort to tug or push on the palm/ finger rest 12 to overcome the friction, the wearer could slidably move the palm/finger rest 12 away from or toward the gauntlet 14, respectively.

The present invention orthosis 10 may optionally be used in combination with an elbow orthosis or cuff 26 (FIG. 2, dashed lines) located at the proximal end of the gauntlet 14. The elbow cuff 26 is configured to stabilize a post-op injured elbow. Such an elbow cuff is disclosed in, for example, U.S. Pat. No. 9,782,285 (Weber) and U.S. Pat. No. 9,737,431 (Weber), the contents of which are incorporated by reference herein.

As seen in FIGS. 1-3, the orthosis 10 preferably includes three retention straps 28, 30, and 32. There may be fewer or more than the three shown. Each strap may be inelastic, but preferably elastic and made of a stretchy mesh or open-knit material for breathability, comfort, and compression of the clamshell on the forearm and wrist. The stretchy, mesh or open-knit straps have a broad width to spread out stress over a larger area that helps control edema. Each end 38 of the straps 28, 30, 31 has the hook VELCRO® component to attach to the softgoods, UBL, or pile fabric of the gauntlet or palm/finger rest. Hand retention strap 28 is stretched and wraps around the palm/finger rest 12 and digits of the patient.

Distal retention strap 30 is stretched and passes through the two thumb openings 18 and preferably crisscrosses at the open top of the clamshell to compress and secure the gauntlet 14 around the wrist. Optional retention loops 34 are located, one each, at the two thumb openings 18. As seen in FIG. 1, the distal retention strap 30 passes through each thumb opening 18 as well as the space between the thumb opening and the retention loop 34, as indicated by the arrow in FIG. 1. The ends 38 of the strap 30 are then attached to the pile exterior of the gauntlet 14.

Finally, an optional proximal strap 32 is stretched and overlies the open top of the clamshell as seen in FIG. 1. The stretchy strap 32 pulls the open top clamshell panels closer together thus compressing the gauntlet 14 around the forearm. The opposite ends 38 of the strap 32 have the VELCRO® hook component that attaches to the softgoods, UBL, or pile fabric exterior of the gauntlet 14. Other strapping systems are contemplated including using laces or strands that have their ends anchored to the gauntlet with hook-and-loop fasteners, claws, eyelets, D-rings, or simple knots; or a longer strap that coils around and circumscribes the gauntlet.

In general, instead of hook-and-loop or VELCRO® type fasteners as the fastening means, it is contemplated that the orthosis use, in the alternative, snaps, laces and eyelets, D-rings, hooks, zippers, buckles or catches with belts, claws, clasps, and the like, or any combination thereof.

While particular forms of the invention have been illustrated and described, it will be apparent that various modifications can be made without departing from the spirit and scope of the invention. It is contemplated that disclosed embodiments and their components may be combined with other disclosed embodiments and their components.

What is claimed is:

1. An elbow-forearm-wrist-hand-finger orthosis for addressing crushed hand injuries, hand fractures, and hand lacerations, comprising:
   a forearm and wrist gauntlet having a clamshell form with a rigid bottom and a proximal end and a distal end, wherein the rigid bottom includes a first curved profile accommodating a wrist neutral application, and the distal end includes at least one thumb opening, and wherein the clamshell includes external hook-and-loop fastener fabric;
   a volar pocket extending along a length of the bottom of the forearm and wrist gauntlet;
   a detachable palm/finger rest partially supporting the palm with a straight, rigid, bar extending proximally therefrom, wherein the bar includes the first curved profile, and the palm/finger rest includes a second curved profile to enable a fingers-relaxed application;
   padding at least partially covering the palm/finger rest;
   a first, open-knit elastic strap disposed about the palm/finger rest overlying and restraining the fingers; and
   a second open-knit elastic strap disposed about the forearm and wrist gauntlet;
   wherein a telescoping slidable coupling between the bar and volar pocket for adjusting a distance of the palm/finger rest from the forearm and wrist gauntlet consists essentially of at least one patch of hook-and-loop fastener anchor disposed on the bar that attaches to a corresponding fastener of the volar pocket of the forearm and wrist gauntlet to maintain the distance of the palm/finger rest from the forearm and wrist gauntlet.

2. The elbow-forearm-wrist-hand-finger orthosis of claim 1, wherein the forearm and wrist gauntlet includes opposed thumb openings for left-hand and right-hand applications.

3. The elbow-forearm-wrist-hand-finger orthosis of claim 2, wherein each thumb opening includes a respective loop, and wherein the second strap passes through each loop and each thumb opening.

4. The elbow-forearm-wrist-hand-finger orthosis of claim 1, wherein the bar is malleable.

5. The elbow-forearm-wrist-hand-finger orthosis of claim 1, wherein the rigid bottom of the forearm and wrist gauntlet is malleable.

6. The elbow-forearm-wrist-hand-finger orthosis of claim 1, wherein the forearm and wrist gauntlet clamshell includes padded panels.

7. The elbow-forearm-wrist-hand-finger orthosis of claim 1, wherein the bottom of the forearm and wrist gauntlet includes a malleable stiffener extending along a length thereof.

8. The elbow-forearm-wrist-hand-finger orthosis of claim 1, wherein the elbow-forearm-wrist-hand-finger orthosis includes an elbow support disposed at the proximal end of the forearm and wrist gauntlet.

9. An elbow-forearm-wrist-hand-finger orthosis for addressing crushed hand injuries, hand fractures, and hand lacerations, comprising:
   a forearm and wrist gauntlet including a semi-rigid clamshell configuration with a bottom and a proximal end and a distal end, wherein the bottom includes an internal stiffener having a first curved profile enabling a wrist neutral application, the distal end includes at least one thumb opening, and the clamshell has an exterior including pile fabric;
   a volar pocket with a distal opening disposed proximate the forearm and wrist gauntlet bottom;
   a detachable palm/finger rest partially supporting the palm with a straight, rigid bar extending proximally therefrom, wherein the palm/finger rest includes a second curved profile to enable a fingers-relaxed application;
   wherein a telescoping slidable coupling between the bar and volar pocket for adjusting a distance of the palm/finger rest from the forearm and wrist gauntlet consists essentially of at least one patch of hook-and-loop fastener anchor disposed on the bar that attaches to a corresponding fastener of the volar pocket of the forearm and wrist gauntlet to maintain the distance of the palm/finger rest from the forearm and wrist gauntlet;

padding at least partially covering the palm/finger rest;
a first elastic strap disposed about the palm/finger rest overlying and restraining the fingers; and
a second elastic strap disposed about the forearm and wrist gauntlet.

10. The elbow-forearm-wrist-hand-finger orthosis of claim 9, wherein the distal end of the gauntlet includes opposed thumb openings for left-hand and right-hand applications.

11. The elbow-forearm-wrist-hand-finger orthosis of claim 10, wherein each thumb opening includes a respective loop, and wherein the second strap passes through each loop and each thumb opening.

12. The elbow-forearm-wrist-hand-finger of claim 9, wherein the clamshell includes a semi-rigid thermoplastic foam at least partially covered in pile fabric.

13. The elbow-forearm-wrist-hand-finger orthosis of claim 9, wherein the palm/finger rest and the straight, rigid bar are formed from an integral piece of rigid material selected from the group consisting of plastic, aluminum, or steel.

14. The elbow-forearm-wrist-hand-finger orthosis of claim 9, wherein the bar is at least partially covered in at least one of softgoods, UBL, and pile fabric.

15. An elbow-forearm-wrist-hand-finger orthosis for addressing crushed hand injuries, hand fractures, and hand lacerations, comprising:
a forearm and wrist gauntlet having a clamshell configuration with a bottom and a proximal end and a distal end, wherein the bottom includes an internal stiffener extending along a length of the clamshell having a first curved profile supporting a wrist neutral application, and the distal end includes at least one thumb opening;
a volar pocket with an opening disposed at the bottom of the forearm and wrist gauntlet;
a palm/finger rest partially supporting the palm with a straight, rigid bar extending proximally therefrom, wherein the palm/finger rest includes a second curved profile for a fingers-relaxed application;
wherein a telescoping slidable coupling between the bar and volar pocket for adjusting a distance of the palm/finger rest from the forearm and wrist gauntlet consists essentially of at least one patch of hook-and-loop fastener anchor disposed on the bar that attaches to a corresponding fastener of the volar pocket of the forearm and wrist gauntlet to maintain the distance of the palm/finger rest from the forearm and wrist gauntlet;
padding at least partially covering the palm/finger rest;
a first elastic strap disposed circumferentially about the palm/finger rest, at least partially overlying and restraining the fingers; and
a second elastic strap disposed circumferentially about the forearm and wrist gauntlet.

16. The elbow-forearm-wrist-hand-finger orthosis of claim 15, wherein the distal end of the clamshell includes opposed thumb openings for left-hand and right-hand applications.

17. The elbow-forearm-wrist-hand-finger orthosis of claim 16, wherein each thumb opening includes a respective loop, and wherein the second strap passes through each loop and each thumb opening.

\* \* \* \* \*